(12) United States Patent
Böger et al.

(10) Patent No.: US 7,883,854 B2
(45) Date of Patent: Feb. 8, 2011

(54) METHOD FOR DETERMINATION OF CARDIOVASCULAR RISK FACTORS IN DRIED BLOOD

(75) Inventors: Gerhild Böger, Hamburg (DE); Kathrin Schwedhelm, Hamburg (DE); Heidemarie Maas, Oldenburg (DE)

(73) Assignee: GermedIQ Forschungs-und Entwickungsellschaft mbH, Hamburg (DE)

( * ) Notice: Subject to any disclaimer, the term of this patent is extended or adjusted under 35 U.S.C. 154(b) by 0 days.

(21) Appl. No.: 11/438,246

(22) Filed: May 22, 2006

(65) Prior Publication Data

US 2007/0077548 A1    Apr. 5, 2007

(30) Foreign Application Priority Data

May 20, 2005   (EP) .................................. 05010944

(51) Int. Cl.
    *G01N 33/53*   (2006.01)
(52) U.S. Cl. ...................... 435/7.1; 435/7.92; 435/7.93; 435/7.94; 436/501; 436/518
(58) Field of Classification Search ...................... 435/6, 435/7.1, 7.92–7.95, 962, 973; 436/501, 518, 436/71, 164, 172–174
    See application file for complete search history.

(56) References Cited

U.S. PATENT DOCUMENTS

| 4,393,134 | A | 7/1983 | Yano et al. | |
| 6,187,531 | B1 | 2/2001 | Tyrrell | |
| 6,309,887 | B1 * | 10/2001 | Ray | 436/67 |
| 2002/0055176 | A1 * | 5/2002 | Ray | 436/67 |
| 2002/0102737 | A1 * | 8/2002 | Millington et al. | 436/94 |
| 2004/0121421 | A1 * | 6/2004 | Han et al. | 435/23 |
| 2005/0048499 | A1 * | 3/2005 | Cerda | 435/6 |
| 2005/0227269 | A1 * | 10/2005 | Lloyd et al. | 435/6 |

FOREIGN PATENT DOCUMENTS

| EP | 1 111 384 A | 6/2001 |
| WO | WO 94/29730 A | 12/1994 |

OTHER PUBLICATIONS

Schulze et al., Determination of asymmetric dimethylarginine (ADMA) using a novel ELISA assay, Clin Chem. Lab Med 2004; 42(12): 1377-1383.*
Nagy et al., Direct tandem mass spectrometric analysis of amino acids in dried blood spots without chemical derivatization for neonatal screening, Rapid Commun. Mass Spectrom. 2003; 17: 983-990.*
Martens-Lobenhoffer et al., Determination of arginine and ADMA in human plasma by LC/MS with the isotope dilution technique, Journal of Mass Spectrometry, 2004; 39: 1287-1294.*
K. Sydow et al., "Homocyst (e) in, endotheliale Dysfunktion . . . " (2001) (Homocyst(e)ine, endothelial dysfunction . . . ) Z. Kardiol, vol. 90, pp. 1-11.
Ridker, "High-Sensitivity C-Reactive Protein . . . ", The American Journal of Cardiology (2003), vol. 92, pp. 17-22.
Schwedhelm et al., "Application of Gas Chromatography-Mass . . . ", Clin Chem Lab Med (2003), vol. 41(12), pp. 1552-1561.
Cordon et al., "C-reactive protein measured in dried blood spots . . . ", Journal of Immunological Methods (1991), vol. 143, pp. 69-72.
Febriani et al., "Determination of total homocysteine in dried blood . . . ", Pediatrics International (2004), vol. 46, pp. 5-9.
Chace et al., "Use of Tandem Mass Spectometry . . . " Clinical Chemistry (2003), vol. 49 (11), pp. 1797-1817.
K. Sydow et al., "ADMA and oxidative stress are responsible for . . . " (2002) Cardiovascular Research 57 (2003), pp. 244-252.
Lemonnier F. et al: "Screening for Familial Hypercholesterolemia by Radioimmunoassay of Apolipoproteins B and A-1 in Dried Blood Spots" International Congress Series, Excerpta Medica, Amsterdam, NL, 1994, pp. 243-246, XP001207809 ISSN: 0531-5131.
Ohta T et al: "Enzyme-Linked Immunosorbent Assay for Apolipoprotein B on Dried Blood Spot Derived from Newborn Infant: Its Application to Neonatal Mass Screening for Hypercholesterolemia" Journal of Pediatric Gastroenterology and Nutrition, Raven Press, New York, NY, US, vol. 7, No. 4, Jul. 1998, pp. 524-531, XP009057743 ISSN: 0277-2116.
Grzeda B R et al: "Development of a Dried Blood Collection, Transport and Testing System for Triglycerides" Clinical Chemistry, American Association for Clinical Chemistry, Washington, DC, US, vol. 48, No. 6, SUPPL, Jun. 2002, p. A106, XP001207808 ISSN: 0009-9147.
Bui Le T et al: "Development of a Dried Blood Collection, Transport and Testing System for HDL-Cholesterol" Clinical Chemistry, American Association for Clinical Chemistry, Washington, DC, US, vol. 48, No. 6, Suppl, Jun. 2002, pp. A103-A104, XP001207807 ISSN: 0009-9147.
Boeger R.H. et al: "Elevated Levels of Asymmetric Dimethylarginine (ADMA) as a Marker of Cardiovascular Disease and Mortality" Clinical Chemistry and Laboratory Medicine, Walter de Gruyter Und Co, DE, vol. 43, No. 10, 2005, pp. 1124-1129, XP009057799 ISSN: 1434-6621.
S. Billecke, et al., "Contribution of whole blood to the control of plasma . . . " AM J Physiol Heart Circ Physiol 291, (2006), pp. H1788-H1796.
Tom Teerlink, "Measurement of asymmetric dimethylarginineinplasma: methodological . . . ", Clin Chem Lab Med (2005), 43(10) pp. 1130-1138.

* cited by examiner

*Primary Examiner*—Melanie J Yu
*Assistant Examiner*—Gary W Counts
(74) *Attorney, Agent, or Firm*—Collard & Roe, PC

(57) ABSTRACT

A method for the determination of cardiovascular risk factors in biological samples that comprising the steps of a) sampling, b) altering the sample into a dry blood sample c) conducting a sample preparation where appropriate and d) analyzing the sample to offer a simple yet effective method for the determination of cardiovascular risk factors in biological samples. It also relates to dry blood filter for performing this method, that filter comprises at least one substance of the group consisting of antioxidants, coagulants, disinfectants, detergents and inhibitors.

5 Claims, No Drawings

METHOD FOR DETERMINATION OF CARDIOVASCULAR RISK FACTORS IN DRIED BLOOD

CROSS REFERENCE TO RELATED APPLICATIONS

Applicants claim priority under 35 U.S.C. §119 of European Application No. 05 010 944.6 filed May 20, 2005.

BACKGROUND OF THE INVENTION

1. Field of the Invention

The present invention is in the field of methods for determination of cardiovascular risk factors and protective factors in biological samples.

2. Description of Related Art

Cardiovascular risk factors include L-arginine (ARG), methylated arginines and lysines, isoprostanes, derivatives and metabolites of isoprostanes, enzymes like matrixmetalloproteinases (MMPs), or vitamins. However, this listing is understood to be exemplary and by no means complete.

Among the cardiovascular risk factors, the methylated arginines and the endogenous inhibitors asymmetric dimethylarginine (ADMA) and monomethyl arginine (MMA) are especially important. Their importance is based on the fact that they are essential for the regulation of nitric oxide (NO) synthesis in the human body. NO in turn is essential in several physiological settings, i.e. homeostasis of the cardiovascular system. Imbalance of NO supply and requirement is regarded as the initial step for pathophysiological changes that eventually lead to cardiovascular diseases like atherosclerosis, hypertension, and thromboembolic disorders. Accumulating evidence suggests that such NO imbalance of homeostasis are mainly linked to ADMA. ADMA and MMA originate from protein arginine methylation, they are released from proteins during protein degradation. Thus far, circulating ADMA was shown to be altered in patients suffering from cardiovascular diseases. Elevated plasma ADMA concentrations are found in various clinical settings ranging from renal failure to atherosclerosis, hypertension diabetes, preeclampsia, alzheimer's disease and even depression or schizophrenia. Moreover, in patients with cardiovascular disease elevated plasma ADMA concentrations independently predict progression of atherosclerosis and mortality.

All currently applied analytical techniques for the determination of cardiovascular risk factors rely upon detection of these factors in plasma, serum and urine specimens. In human blood and urine specimens, the parameters ARG, ADMA, SDMA and MMA together with the biochemical parameters such as C-reactive protein (CRP), isoprostanes, MMPs, Myeloperoxidase, HDL, LDL or total cholesterol have been evaluated to assess cardiovascular risk (Sydow: *Z Kardiol* 2001, Böger: *Cardiovasc Res* 2003, Ridker: *Am J Cardiol* 2003, Schwedhelm: *Clin Chem Lab Med* 2003). However, using human blood requires rapid separation of cellular blood constituents to obtain serum or plasma and thereby avoiding sample degradation. Thus, sample preparation steps are required which necessitate further equipment at the site of sample collection, such like centrifuges, pipettes, refrigerators, etc. The need of sample preparation makes the sampling elaborate and time-consuming.

The most efficient and precise methods utilized today for quantifying ARG and its methylated analogs are based on LC-MS or LC-MS/MS, although various other methods for determination of these important cardiovascular risk factors have been developed: spectrophotometry, capillary electrophoresis, liquid chromatography, GC-MS or immunoassays like ELISA. Equipment for LC-MS or LC-MS/MS is only available in few large laboratories. Thus, human blood samples commonly have to be shipped from physicians offices or pharmacies to the laboratory which results in samples to be sent in frozen state and which renders the step of sample preparation crucial for the quality of the analysis.

Due to the importance of ARG and its methylated analogs as cardiovascular risk factors, there is a need for a robust method of sample preparation which avoids degradation of analytes prior to quantitation in the clinical chemical laboratory and which allows a large number of samples to be routinely measured.

SUMMARY OF THE INVENTION

It is therefore object of the invention to overcome the limitations of the state of the art and to develop a simple yet effective method for the determination of cardiovascular risk factors in biological samples.

It is a further object of the invention to offer appropriate means for conducting the simple yet effective method.

The first object of the invention is solved by the fact that the method comprises the steps of a) sampling, b) altering the sample into a dry blood sample, c) conducting a sample preparation where appropriate and d) analyzing the sample. Especially altering the sample into a dry blood sample solves the first object of the invention. Dry blood samples as such are known since R. Guthrie used filters to collect and dry human blood of newborns for subsequent analysis of phenylalanine for the detection of phenylketonuria (PKU). Since then, the use of dry blood specimen has been extended from newborn screening to virological and epidemiological research. Dry blood has been used for the detection of disorders of amino acid metabolism, fatty acid and organic acid metabolism, for monitoring infection and effectiveness of antibiotic treatment (CRP in dried blood spots from patients with cystic fibrosis, Cordon S M: *J Immunol Methods* 1991), homocystinuria (homocysteine in dried blood spots from newborns; Febriani A D: *Pediatr Int* 2004) and PKU (amino acids/acylcarnitines in dried blood spots from newborns; Chace D H: *Clin Chem* 2003).

Dry blood specimen have never been used for the combined determination of cardiovascular risk factors before.

This is mainly to the nature of the investigated analytes and the underlying scientific problems. With regard to newborn screening or to disorders of amino acid metabolism, it is more important to obtain the qualitative information about the presence or absence of a single analyte than to obtain an exact quantitative information about the absolute concentration which requires elaborate knowledge and techniques. Furthermore, the analytes in the state of the art determinations exhibit a rather high concentration compared to cardiovascular risk factors like ADMA. For example, ADMA concentration are typically around 0.5 µmol/l whereas phenylalanine is found to be 30-100 µmol/L in healthy children as compared to 1.2 mmol/L in patients with phenylketonuria. That is to say, such screening as it is used by the state of the art using dry blood requires differentiation of 10- to 60-fold increases in the analyte. In contrast, cardiovascular risk factors such like ADMA may be elevated by a factor as little as 1.3-1.5 and still indicate an elevated risk, making elaborate adjustments of the state of the art necessary such as they are described in the present invention to compensate for this.

A person skilled in the art would not have taken into account the use of dry blood for the determination of cardiovascular risk factors, especially ADMA. The reason for this is that during the drying process of the blood sample, the concentration of ADMA in the plasma changes due to a partial lysis of the blood cells leading to a release of ADMA formerly contained in the cells. Since the concentration of various analytes in plasma or serum is different to that in blood cells, such a lysis would lead to wrong or varying values of the plasma or serum concentrations of ADMA. Therefore, the person skilled in the art would have relied on plasma or serum samples for the determination of the ADMA concentration. Furthermore, a dried blood spot is in general a highly imprecise specimen compared with liquids such as blood, plasma or urine. This is due to the fact that the quantity of blood in the blood spot is a function of hematocrit, diameter of the blood spot, degree of saturation and degree of haemolysis. Typically, a blood spot before drying has a volume of only 20 to 40 µl. Using dry blood specimen would have complicated the measurement of the cardiovascular risk factors.

Particularly, if step b) of the inventive method comprises the complete haemolysis of the whole blood sample and/or an inhibition of enzymes and/or an inhibition of proteolytic activity and/or a hindrance of oxidation, the disadvantage of wrong or varying values of the plasma/serum concentrations of the analytes is advantageously avoided. Allowing the sample to undergo a complete haemolysis is in contrast to the state of the art, since haemolysis is regarded generally as a source of error and therefore the state of the art methods thoroughly try to avoid it. In contrast to this conception, the inventive allowance of complete haemolysis of the blood sample results in advantageously stable values. The reason for this is that the invention changes the reference basis for the calculation of the ADMA concentration. By virtue of controlled haemolysis, for example by use of a detergent substance like Triton X100, the ADMA contained in the blood cells is released, so that the sum of ADMA concentrations in plasma and in blood cells is advantageously determined. This results in higher ADMA concentrations, reducing the requirements for the used detection method. This change of the reference basis allows a more precise measurement of the accurate ADMA concentration. From a scientific point of view, the change in the reference basis for the calculation is admissible. Independent from its origin, ADMA shows physiological effects and moreover, ADMA contained in plasma may be merely a "spill-over" of the ADMA retained in cells.

Many compounds studied as risk factors tend to degrade if kept at room temperature or under air. Determination of ARG in human blood samples is possible with higher correctness, if ARG degrading enzymes like arginases are inhibited during step b) of the inventive method. The presence of arginases lead to rapid decline of ARG concentrations especially when the sample is stored at room temperature. This also occurs in the drying process and may lead to false low values. Advantageously, by use of arginase inhibitors such as, but not limited to, nor-N-hydroxyarginine (nor-NOHA) there will be an inhibition of enzymes. For example, the use of 20 µM nor-NOHA is sufficient to block degradation of L-arginine and does not interfere with subsequent determination of L-arginine, ADMA or SDMA by LC-MS or ELISA. The inhibitation of oxidation, especially the ex vivo oxidation of markers of oxidative stress like isoprostanes and their metabolites, will advantageously lead to stable and precise measurements. Oxidation may effectively be inhibited by use of antioxidant substances like α-hydroxy-TEMPO and/or EDTA. As methylated arginines are derived from protein methylation with subsequent proteolytic breakdown, it is important to inhibit proteolytic activity in the sample as well. This may be achieved by using a protease inhibitor such as but not limited to [final concentrations]: 1 mM aprotinin 0.15 units/ml+leupeptin 5 µg/mL (10 µM), pepstatin 1 µg/mL, sodium fluoride 1 mM.

In general, a "sample" encompasses a variety of sample types obtained from an individual and can be used in a diagnostic or monitoring sense. The definition encompasses blood, blood-derived samples and other liquid samples of biological origin, tissue samples such as a biopsy specimen or tissue cultures or cells derived therefrom and the progeny thereof. That also includes samples that have been manipulated in any way after their procurement, such as by treatment with reagents, solubilization, or enrichment for certain components. It encompasses clinical samples and also cells in culture, cell supernatants, cell lysates, serum, plasma, cerebrospinal fluid, urine, saliva, biological fluid tissue samples, and dietary compounds and products.

The cardiovascular risk factors to be determined is ADMA and/or SDMA and/or a combination of ADMA and/or SDMA with at least one substance of the group consisting of MMA, ARG, methylated lysines, isoprostanes, derivatives and/or metabolites of isoprostanes, enzymes, vitamines, C-reactive protein, oxLDL, B-type natriuretic peptide (BNP), NT-pro-BNP, homocysteine or troponin T. Up to now, only single risk factors are determined to investigate the absence or presence of a single disease. By determining in a sample more than one risk factor simultaneously the invention offers the advantageous possibility of obtaining a more reliable proposition of the likeliness of a cardiovascular disease. Such scores of factors or markers are only known in a qualitative way, for example overweight and smoking are scores for cardiovascular diseases. Moreover, the inventive method can easily be adapted to assess ADMA in combination with other cardiovascular risk factors or protective factors in various body fluids including blood, urine and saliva.

In an embodiment of the invention, step d) is performed by use of at least one of the following measurement techniques: mass spectrometry, preferably tandem mass spectrometry, immunoassay, preferably enzyme or radio immunoassay, fluorescence based assay, chemiluminescence based assay. Advantageously, the present invention enables a combination of the above mentioned precise, selective and sensitive measurement techniques with the low expenditure sample preparation according to the invention. However, in particular when assuming a progress in analytical technology, other techniques may also allow for the assessment of methylated arginines and other cardiovascular risk factors as those mentioned above in dried blood specimens.

Depending upon the nature of the samples, a sample preparation is provided, preferably consisting of a protein precipitation, particularly a solvent precipitation which is easy to handle and not disturbing the subsequent quantitation. Preferably, this optional step is automated. Automation can be achieved by using any method known to the person skilled in the art.

The second object of the invention is solved by a dry blood filter for performing the method described above, that comprises at least one substance of the group consisting of antioxidants, coagulants, disinfectants, detergents and inhibitors. As mentioned above, these substances advantageously hinder a degradation or alteration of the sample. Furthermore, addition of a disinfectant to the filter paper allows shipment of dried blood spots originating from potentially infectious material spots by ordinary mail service. Such disinfectants may comprise, but are not limited to phenol and its derivatives like thymol, o-polyphenol; Cationic compounds like benzalconium chloride, chlorhexidine; aldehydes like formaldehyde or others and alcohols such like n-propanol.

In cases in which a separation of the blood cells from the blood is desired to avoid liberation of intracellular compounds from lysing or damaged cells and not a complete haemolysis, a filter according to the invention comprises pores with unequal pore sizes for separating blood cells from plasma. Due to their larger diameter, blood cells exhibit a different permeability compared to plasma.

A simple solution to this problem is the use of different types of filter paper and membranes which are not permeable to blood cells causing a separation of the cells and plasma by means of chromatography, filtration or capillary forces. For example the filter spot in the center of the dry blood filter is permeable to blood cells while the surrounding paper is not.

Impregnating the filter paper with a substance leading to rapid coagulation/clotting without lysis and destruction of the blood cells and the additional used of a simple color indicator that allows later identification of areas of filter paper outside the blood clot where only cell free blood (plasma/serum) "diffused". By this method areas of filter paper impregnated only by cell free plasma could be easily generated and identified.

The inventive combination of high-end analysis techniques with low expediture dry blood samples allow an inventive method for conducting cardiovascular risk factor screening tests which comprising the steps of a) sampling and altering the sample in a dry blood sample at the sampling site, b) shipping of the dry blood sample to an analysis site, c) analyzing the dry blood sample at the analysis site and d) transmitting the results to the sampling site for further usage. Advantageously, the sampling site need not to be equipped with expensive analytical apparatus, sampling and sample preparation are easy to handle and there is no need for taking special security precautions during shipping. The dry blood filters may be send by normal mail, even if hazardous substances are contained in the sample. Furthermore, due to the centralization of analysis, the operators at the few analysis sites have the technological expertise to guarantee for most precise and accurate measurements.

DETAILED DESCRIPTION OF PREFERRED EMBODIMENTS

The following examples describe two embodiments of the invention.

Example 1

Capillary blood was collected and directly transferred to specimen collection paper (Schleicher&Schuell, 903™). The filter paper was dried and a 3 mm (diameter) circle was punched out. Analytes were eluted from the filter paper with 100 µl methanol containing internal standard. The eluates were filtered through a 0.22 mm filter membrane and dried. Analytes were subsequently converted to their butyl ester derivatives. In brief, 60 µL of acetyl chloride in 1-butanol (1:10, vol/vol) were added and heated to 65° C. for 17 min. After completed reaction, butyl ester derivatives were dried again and reconstituted in 200 µL methanol/water (1:1, vol/vol) and subjected to mass spectrometric analysis. Mass spectrometric analysis was performed on a TSQ Quantum Discovery MAX (Thermo Electron, Dreieich, Germany) LC-ESI-MS/MS system. 15 µL of samples were injected via loop (50 µL loop) without any column used. Acetonitrile/water (80:20, vol/vol) containing 0.1% formic acid was pumped isocratic at 0.2 mL/min at ambient temperature (23° C.). Total run time was 2 min. Nitrogen was used as the nebulizing and drying gas (350° C.). For ionisation in the positive electrospray ionisation (ESI+) needle and shield voltage were set to 5000 and 400 Volts, respectively. Fragmentation of analytes was monitored (selected-reaction monitoring, SRM) after collision induced activation (CIA) with argon (1.0 mTorr): mass-to-charge (m/z) ratio 231 to m/z 70 at 24 eV for L-arginine, m/z 259 to m/z 228 at 18 eV for SDMA, m/z 259 to m/z 214 at 18 eV for ADMA, and, m/z 265 to m/z 220 at 18 eV for internal standard (hexadeuterated ADMA). The ADMA levels were found to be 0.91+/−0.2 µM, SDMA levels were found to be 0.32+/−0.08 µM (n=10).

Example 2

Capillary blood was collected and directly transferred to specimen collection paper (Schleicher&Schuell, 903™). The filter paper was dried and a 5 mm (diameter) circle was punched out. Analytes were eluted from the filter paper with 200 µL methanol/water, 10:90, vol/vol. The eluates were dried under nitrogen and reconstituted in 50 µL water. Samples were centrifuged at 2000×g and 20 µL of the supernatant were analyzed using a commercially available ELISA assay according to the manufacturer's instructions (DLD Diagnostika GmbH). In brief, 20 µL of sample were transferred into the wells of a 96-well reaction plate. Acylation buffer (25 µL), and the adjustment buffer (25 µL), were added to each well. The reaction plate was incubated for 30 minutes at room temperature and adjustment buffer (1.5 mL) was added to each well. The reaction plate was again incubated for 45 minutes at room temperature. An aliquot (50 µL) of the pre-treated samples was transferred into the wells of the microtitre plate and the antiserum solution (50 µL) was added to each well. The microtitre plate was subsequently incubated for 15-20 hours at 2-8° C. After incubation the solution from each well was removed and the wells were washed with wash buffer (250 µL) four times. Subsequently the solution of enzyme conjugate (100 µL) was added to each well and the microtitre plate was incubated for one hour at room temperature on a horizontal shaker. Then the wells were again washed four times with the wash buffer. After washing substrate solution (100 µL) was added and the microtitre plate was incubated for 20-30 minutes. The reaction was stopped and the optical density was read at 450 nm (reference wave length 570-650 nm). The ADMA levels found were 0.74+/−0.09 µM (n=5).

The invention claimed is:

1. A method for determining cardiovascular risk factors in a biological sample comprising the steps of:
    (a) collecting a biological sample from a person;
    (b) altering the biological sample to obtain a dry blood sample; wherein step b) comprises a complete haemolysis of the biological sample controlled by a detergent substance; and
    (c) analyzing the dry blood sample to make a quantitative determination of a cardiovascular risk factor by at least one measurement technique selected from the group consisting of mass spectrometry, immunoassay, fluorescence based assay, and chemiluminescence based assay, the quantitative determination determining concentration of the cardiovascular risk factor in the dry blood sample;
    wherein the cardiovascular risk factor to be determined is at least one member selected from the group consisting of asymmetric dimethylarginine, symmetric dimethylarginine, and a combination of asymmetric dimethylarginine or symmetric dimethylarginine with at least one substance of the group consisting of monomethyl arginine, L-arginine, methylated lysines, isoprostanes, derivatives of isoprostanes, metabolites of isoprostanes, enzymes, vitamines, C-reactive protein, oxidized low-density lipoprotein, B-type natriuretic peptide, N-terminal pro B-type natriuretic peptide, or troponin T;
    wherein the biological sample is a whole blood sample; and wherein the detergent substance is Triton X-100.

2. The method according to claim 1,
wherein step c) is performed by use of at least one of the following measurement techniques: tandem mass spectrometry, enzyme immunoassay, and radio immunoassay.

3. The method according to claim 1,
wherein step b) comprises at least one of an inhibition of enzymes, an inhibition of proteolytic activity, and a hindrance of oxidation in addition to complete haemolysis of the biological sample.

4. The method according to claim 1,
further comprising the step of precipitating proteins to purify the sample for subsequent quantitative analysis.

5. The method according to claim 1,
further comprising filtering the biological sample prior to altering the biological sample according to steps b) and c) to separate blood cells from plasma.

* * * * *

UNITED STATES PATENT AND TRADEMARK OFFICE
CERTIFICATE OF CORRECTION

PATENT NO.         : 7,883,854 B2
APPLICATION NO.    : 11/438246
DATED              : February 8, 2011
INVENTOR(S)        : Böger et al.

It is certified that error appears in the above-identified patent and that said Letters Patent is hereby corrected as shown below:

In particular, on the cover page, column 1, item [73], please change "GermedIQ Forschungs-und Entwickungsellschaft mbH" to correctly read:

--GermedIQ Forschungs-und Entwicklungsgesellschaft mbH--.

Signed and Sealed this
Twenty-second Day of March, 2011

David J. Kappos
*Director of the United States Patent and Trademark Office*